(12) United States Patent
Pryor et al.

(10) Patent No.: US 8,292,497 B2
(45) Date of Patent: Oct. 23, 2012

(54) CLOUD POINT MONITORING SYSTEMS FOR DETERMINING A CLOUD POINT TEMPERATURE OF DIESEL FUEL

(75) Inventors: Bryan K. Pryor, Farmington, MI (US); William C. Albertson, Clinton Township, MI (US); Mike M. McDonald, Macomb, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 1113 days.

(21) Appl. No.: 12/173,990

(22) Filed: Jul. 16, 2008

(65) Prior Publication Data

US 2010/0012410 A1    Jan. 21, 2010

(51) Int. Cl.
*G01N 25/12*    (2006.01)
*G01N 25/36*    (2006.01)
*G01N 25/14*    (2006.01)

(52) U.S. Cl. ............ 374/19; 374/141; 374/147; 374/28; 374/135; 374/144

(58) Field of Classification Search ...... 703/2; 700/300; 73/627, 23.25, 25.01, 25.04, 29.01, 29.02; 250/335; 62/498, 159; 374/16, 17, 18, 19, 374/20, 21, 22, 23, 24, 25, 26, 27, 28, 144, 374/141, E11.001, E13.001, 120, 121, 43, 374/45, 135, 147, 130–132; 340/584; 702/1
See application file for complete search history.

(56) References Cited

U.S. PATENT DOCUMENTS

| | | | | |
|---|---|---|---|---|
| 4,519,717 A * | 5/1985 | Jones et al. | ...................... | 374/17 |
| 4,759,637 A * | 7/1988 | Baillie | ............................. | 374/28 |
| 4,760,538 A * | 7/1988 | Bock et al. | ..................... | 702/136 |
| 4,946,288 A * | 8/1990 | Siska et al. | ....................... | 374/20 |
| 5,007,733 A * | 4/1991 | Laurent et al. | .................. | 356/70 |
| 5,088,833 A * | 2/1992 | Tsang et al. | .................... | 374/17 |
| 5,651,614 A | 7/1997 | Juneau | | |
| 6,022,138 A * | 2/2000 | Sonander | ........................ | 374/28 |
| 6,827,484 B2 | 12/2004 | Tsang et al. | | |
| 6,966,692 B2 * | 11/2005 | Tsang et al. | .................... | 374/20 |
| 7,155,347 B2 * | 12/2006 | Going et al. | .................... | 702/31 |
| 2005/0053116 A1 * | 3/2005 | Tsang et al. | .................... | 374/20 |
| 2007/0147467 A1 * | 6/2007 | Arnold et al. | ................... | 374/28 |
| 2008/0237503 A1 * | 10/2008 | Albertson | ..................... | 250/564 |
| 2010/0014553 A1 * | 1/2010 | Pryor et al. | ..................... | 374/16 |
| 2010/0014554 A1 * | 1/2010 | Albertson | ....................... | 374/16 |
| 2011/0188535 A1 * | 8/2011 | Boehm | ........................... | 374/20 |
| 2012/0044968 A1 * | 2/2012 | Haran et al. | .................... | 374/17 |
| 2012/0069866 A1 * | 3/2012 | Derevyagin et al. | ............ | 374/28 |

FOREIGN PATENT DOCUMENTS

JP    61132849 A *    6/1986

* cited by examiner

*Primary Examiner* — Gail Verbitsky
(74) *Attorney, Agent, or Firm* — Cantor Colburn LLP (57) ABSTRACT

Cloud point monitoring systems for determining a cloud point temperature value for diesel fuel are provided. In one exemplary embodiment, a cloud point monitoring system receives diesel fuel in the tubular conduit and propagates light through the diesel fuel. The cloud point monitoring system further determines a cloud point temperature value indicative of a cloud point of the diesel fuel based on a light intensity level of the light that has propagated through cooled diesel fuel.

20 Claims, 5 Drawing Sheets

CLOUD POINT MONITORING SYSTEMS FOR DETERMINING A CLOUD POINT TEMPERATURE OF DIESEL FUEL

FIELD OF THE INVENTION

Exemplary embodiments of the present invention relate generally to diesel fuel systems, and more particularly to diesel fuel cloud point monitoring systems.

BACKGROUND

At relatively cold ambient temperatures diesel fuel can partially solidify (gel) due to the formation of waxy crystals. Gelling of the fuel can effect engine performance, including causing the engine to cease operation. Formation of the waxy crystals causes the fuel to become cloudy. The cloud point temperature of the fuel is the temperature at which the wax crystals begin to form. The cloud point temperature of diesel fuel can vary widely even within fuel of the same grade (i.e., No. 2 diesel), and also varies widely when biodiesel fuels are mixed with diesel fuel. Diesel fuels are generally blended so as to have a cloud point temperature which is appropriate for the location in which the fuel is sold. Therefore, it may be desirable to detect and monitor the cloud point temperature of the diesel fuel, since vehicles may take on fuel in a relatively warmer region where gelling is not a concern and due to their long travel range carry the fuel blended for the warmer region to relatively colder regions where gelling is possible. A problem associated with some existing cloud point monitoring devices is that wax crystals can form in such a way that they may not be detected in the diesel fuel, resulting in an inaccurate determination of the cloud point temperature, thereby limiting the ability to take appropriate measures to prevent gelling of the diesel fuel.

Accordingly, it is desirable to develop cloud point monitoring systems having improved accuracy with regard to detection and monitoring of the cloud point temperature.

SUMMARY OF THE INVENTION

A cloud point monitoring system in accordance with an exemplary embodiment is provided. The cloud point monitoring system includes a first conduit having a first aperture and a second aperture, and is operative for a portion of diesel fuel supply to enter the first aperture, flow in the first conduit and exit the second aperture. The cloud point monitoring system further includes a light source disposed in the first conduit. The light source is configured to emit light in the first conduit in response to a first signal. The cloud point monitoring system further includes a light sensor disposed in the first conduit. The light sensor is configured to receive at least a portion of the light and to generate a second signal indicative of a light intensity level. The cloud point monitoring system further includes a temperature sensor configured to generate a third signal indicative of a temperature of the diesel fuel in the first conduit. The cloud point monitoring system further includes a controller configured to generate the first signal to induce the light source to emit light. The controller is further configured to receive the second signal from the light sensor and the third signal from the temperature sensor and to determine a cloud point temperature value associated with the diesel fuel based on the second and third signals.

A motor vehicle in accordance with another exemplary embodiment is provided. The motor vehicle includes a diesel engine configured to receive diesel fuel from a fuel tank. The motor vehicle further includes a cloud point monitoring system receiving a portion of the diesel fuel from the fuel tank. The cloud point monitoring system includes a first conduit having a first aperture and a second aperture and is operative such that the portion of diesel fuel enters the first aperture, flows in the first conduit and exits the second aperture. The cloud point monitoring system further includes a light source disposed in the first conduit. The light source is configured to emit light in the first conduit in response to a first signal. The cloud point monitoring system further includes a light sensor disposed in the first conduit. The light sensor is configured to receive at least a portion of the light and to generate a second signal indicative of a light intensity level. The cloud point monitoring system further includes a temperature sensor configured to generate a third signal indicative of a temperature of the portion of the diesel fuel in the first conduit. The cloud point monitoring system further includes a controller configured to generate the first signal to induce the light source to emit light. The controller is further configured to receive the second signal from the light sensor and the third signal from the temperature sensor and to determine a cloud point temperature value associated with the diesel fuel based on the second and third signals.

BRIEF DESCRIPTION OF THE DRAWINGS

Other features, advantages and details appear, by way of example only, in the following description of embodiments, the description referring to the drawings in which.

DESCRIPTION OF THE EMBODIMENTS

Figure 1:
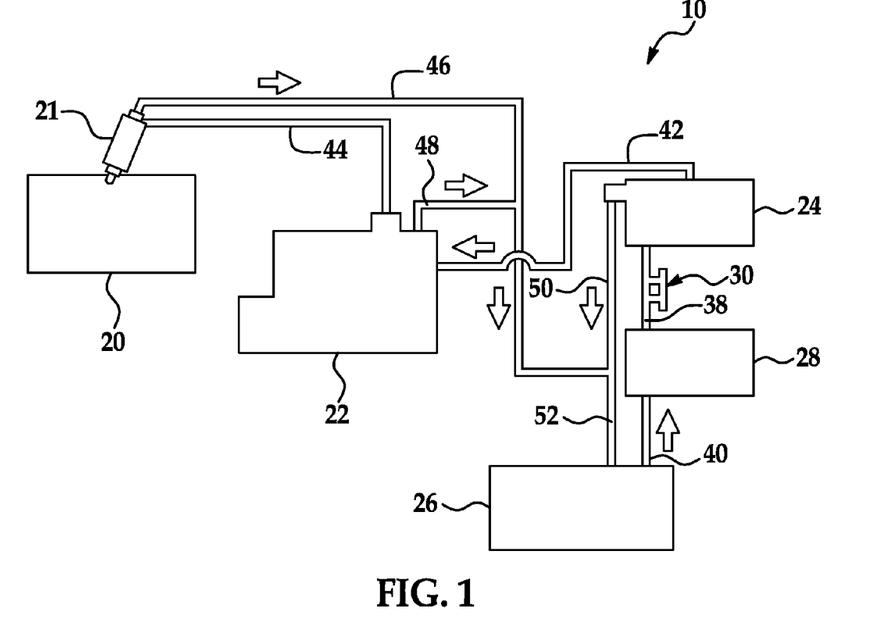
FIG. 1 is a schematic of a vehicle having a cloud point monitoring system in accordance with an exemplary embodiment of the invention.

Referring to FIG. 1, a motor vehicle 10 having a cloud point monitoring system 30 in accordance with an exemplary embodiment is provided. The motor vehicle 10 further includes an engine 20, a fuel injector 21, a fuel pump 22, a fuel filter 24, a fuel tank 26, a feed pump 28, tubular fuel conduits 40, 42, 44, 46, 48, 50, 52 which fluidly interconnect various of the aforementioned components for communication of diesel fuel between them, and a diesel fuel conduit 38. Conduits 38, 42, 44, 46, 48, 50 and 52 are described herein as tubular conduits, but any suitable conduit may be employed, including conduits of other cross-sectional shapes. Associated with diesel fuel conduit 38 is a cloud point monitoring system 30 which is provided to determine and monitor a cloud point temperature for diesel fuel utilized by the vehicle 10. While cloud point monitoring system 30 is associated with diesel fuel conduit 38 in the exemplary embodiments shown, association with other tubular conduits of a fuel system is also believed to be possible and within the scope of the present invention. Further, while illustrated in the various exemplary embodiments described herein in conjunction with engine 20 for vehicle 10, cloud point monitoring system 30 may be employed in fuel systems for all manner of diesel engines.

The fuel injector 21, fuel pump 22, fuel filter 24, fuel tank 26, fuel pump 28, tubular conduits 40, 42, 44, 46, 48, 50 and 52, diesel fuel conduit 38 and monitoring system 30 are elements of a fuel system for delivering diesel fuel to engine 20. The feed pump 28 fluidly communicates with the tubular conduit 40 and the diesel fuel conduit 38. The feed pump 28 is configured to pump diesel fuel from the fuel tank 26 through the tubular conduit 40 and the diesel fuel conduit 38 to the fuel filter 24.

The fuel filter 24 fluidly communicates with the diesel fuel conduit 38 and the tubular conduits 42, 50. The fuel filter 24 is configured to filter the diesel fuel flowing therethrough and to allow a portion of the diesel fuel to flow through the tubular conduit 42 to the fuel pump 22. The fuel filter 24 is further configured to return a portion of the received diesel fuel through the tubular conduits 50, 52, to the fuel tank 26.

The fuel pump 22 fluidly communicates with the tubular conduits 42, 44 and 48. The fuel pump 22 is configured to pump diesel fuel through the tubular conduit 44 to the fuel injector 21. The pressure of the diesel fuel within the tubular conduit 44 is at a relatively high pressure level. The diesel pump 22 is further configured to return some residual diesel fuel through the tubular conduits 48, 52 to the fuel tank 26.

The fuel injector 21 is operably coupled to the engine 20 and fluidly communicates with the tubular conduits 44, 46. The fuel injector 21 is configured to receive diesel fuel from the fuel pump 22 via the tubular conduit 44 at a relatively high pressure level. The fuel injector 21 is further configured to inject a first portion of the received diesel fuel into the engine 20. A second portion of diesel fuel received by the fuel injector 21 is routed through the tubular conduits 46, 52 back to the fuel tank 26.

Before providing a detailed explanation of the cloud point monitoring system 30, a general overview of diesel fuel and detection of the cloud point temperature will be discussed. In particular, when diesel fuel is at or below a cloud point temperature, wax crystals form in the diesel fuel. The cloud point temperature may vary during use of the fuel system and engine 20 upon refueling, the addition of various fuel additives and other factors. Further, if a light source transmits light through the diesel fuel having the wax crystals, a portion of the light is dispersed by reflection off the wax crystals or otherwise. In this situation, only a portion of the light emitted or transmitted by the source may reach a light sensor disposed away from the light source. In accordance with the present invention, the formation of wax crystals can be detected by monitoring an amount of emitted or transmitted light being received by a light sensor disposed away from the light source.

Figure 2:
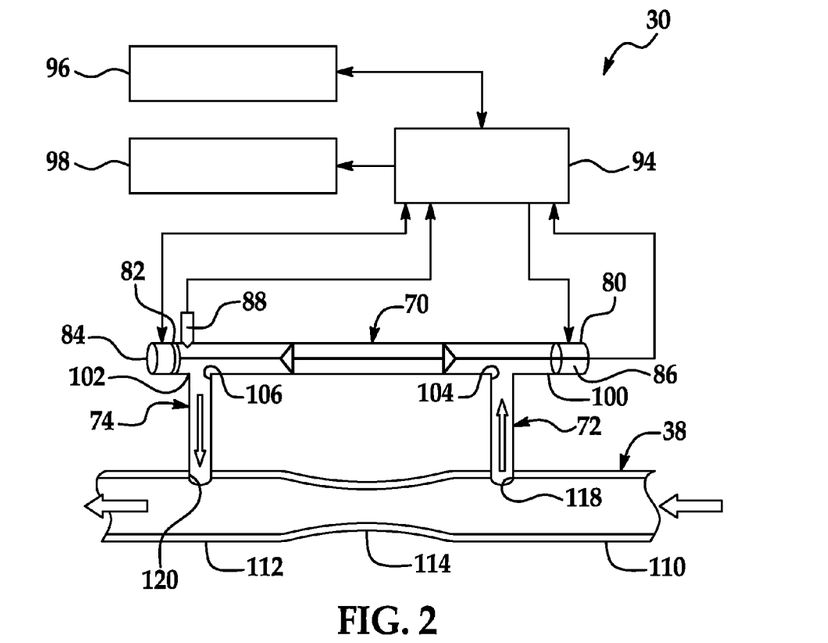
FIG. 2 is a schematic illustration of the cloud point monitoring system of FIG. 1.

Referring to FIG. 2, the cloud point monitoring system 30 which determines a cloud point temperature of diesel fuel will now be explained in greater detail. The cloud point monitoring system 30 includes tubular conduits 70, 72, 74, a light source 80, a reflective member 82, a thermal device 84, a light sensor 86, a temperature sensor 88, a controller 94, a memory device 96, and a display device 98. The cloud point monitoring system 30 is fluidly coupled to the diesel fuel conduit 38 and receives a portion of the diesel fuel flowing through the diesel fuel conduit 38, to determine the cloud point temperature of the diesel fuel. References made herein to various tubular conduits will be understood to include any suitable conduit shape and cross-section, including various non-circular cross-sections.

The tubular conduit 72 is disposed between the diesel fuel conduit 38 and the tubular conduit 70. The tubular conduit 72 is configured to receive a portion of the diesel fuel flowing through diesel fuel conduit 38 via the aperture 118 in the end portion 110 of the diesel fuel conduit 38 and to route this portion of the diesel fuel through the aperture 104 of the tubular conduit 70 into the tubular conduit 70. The aperture 104 is disposed proximate to the first end 100 of the tubular conduit 70.

The tubular conduit 74 is disposed between the diesel fuel conduit 38 and the tubular conduit 70. The tubular conduit 74 is configured to receive the portion of diesel fuel in tubular conduit 70 via the aperture 106 in the second end 102 of the tubular conduit 70 and to route this portion of the diesel fuel through the aperture 120 of the diesel fuel conduit 38 back into the diesel fuel conduit 38. The aperture 106 is disposed proximate the second end 102 of the tubular conduit 70. The tubular conduit 70 is provided to allow diesel fuel to flow therethrough. The tubular conduit 70 has the first end 100 and the second end 102. Diesel fuel flows from the first end 100 toward the second end 102.

The light source 80 is coupled to the tubular conduit 70 proximate to the first end 100 of the tubular conduit 70. The light source 80 is configured to transmit light, preferably as a focused or coherent light beam, through the tubular conduit 70, in response to receiving a signal from the controller 94. The light source 80 can comprise any device that can transmit visible light or non-visible light. In one exemplary embodiment, the light source 80 is a laser that emits coherent light. In other exemplary embodiments, light source 80 can be one of a light emitting diode (LED), an incandescent light and a fluorescent light. Light source may also incorporate various lenses or other means for focusing the transmitted light.

The reflective member 82 is coupled to the tubular conduit 70 proximate to the second end 102 of the tubular conduit 70. The reflective member 82 is configured to receive a portion of the light transmitted from the light source 80 and to reflect the portion of light received from second end 102 toward the first end 100 of the tubular conduit 70. In one exemplary embodiment, the reflective member 82 is a mirror.

The thermal device 84 is disposed proximate second end 102 and reflective member 82 adjacent to the tubular conduit 70. The thermal device 84 is configured to cool the tubular conduit 70 and the diesel fuel therein, in response to receiving a control signal from the controller 94. In one exemplary embodiment, the thermal device 84 is a Peltier cell; however, other suitable means for cooling may also be employed within the scope of the present invention.

The light sensor 86 is coupled to the tubular conduit 70 proximate to the first end 100 of the tubular conduit 70. The light sensor 86 is configured to receive light from the reflective member 82 and to generate a signal indicative of a light intensity level associated with the received light. The signal from the light sensor 86 is sent to the controller 94. Any light sensor 86 suitable to detect the light emitted by light source 80 may be used. In one exemplary embodiment, light sensor 86 comprises a photo-sensitive diode or transistor.

The temperature sensor 88 is disposed on the tubular conduit 70 and fluidly communicates with the diesel fuel within the tubular conduit 70. The temperature sensor 88 is configured to generate a signal indicative of a temperature of the diesel fuel in the tubular conduit 70, which is received by the controller 94. In one exemplary embodiment, temperature sensor 88 comprises a thermocouple.

The controller 94 is electrically coupled to and operative for signal communication with the light source 80, the thermal device 84, the light sensor 86, and the temperature sensor 88. The controller 94 is provided to determine a cloud point temperature of the diesel fuel based on signals received from the temperature sensor 88 and the light sensor 86, as will be explained in greater detail below. In one exemplary embodiment, the controller 94 comprises a microprocessor. The memory device 96 is provided to store data and values generated by the controller 94 therein. The display device 98 is provided to display data and values generated by the controller 94.

The diesel fuel conduit 38 includes the end portion 110, the end portion 112, and a restricted portion 114. The restricted portion 114 is disposed between the end portions 110, 112. The restricted portion 114 causes a pressure drop in the diesel conduit 38 which induces diesel fuel to flow from end portion 110 to end portion 112 through the tubular conduits 72, 70 and 74. The restricted portion 114 of fuel conduit 38 acts as a flow induction mechanism to induce flow of a portion of the fuel supply available in conduit 38 through conduits 72, 70 and 74.

The cloud point monitoring system 30 of the present invention is particularly advantageous in that it enables measurement of the cloud point temperature of the fuel in a conduit which is similar to conduits used throughout the fuel system and under similar fluid flow conditions, thereby reducing or eliminating any effect of the fluid flow conditions, particularly quiescent conditions, on the measurement of the cloud point temperature. However, cloud point monitoring system 30 is in a separate branch of the fuel system and associated fuel conduits such that the process of monitoring and the formation of waxy crystals will have minimal impact on the performance of the fuel system. For example, any reduction in flow associated with monitoring and the formation of waxy crystals in the fuel will only affect flow through the cloud point monitoring system 30 and not the overall fuel system.

Figure 3:
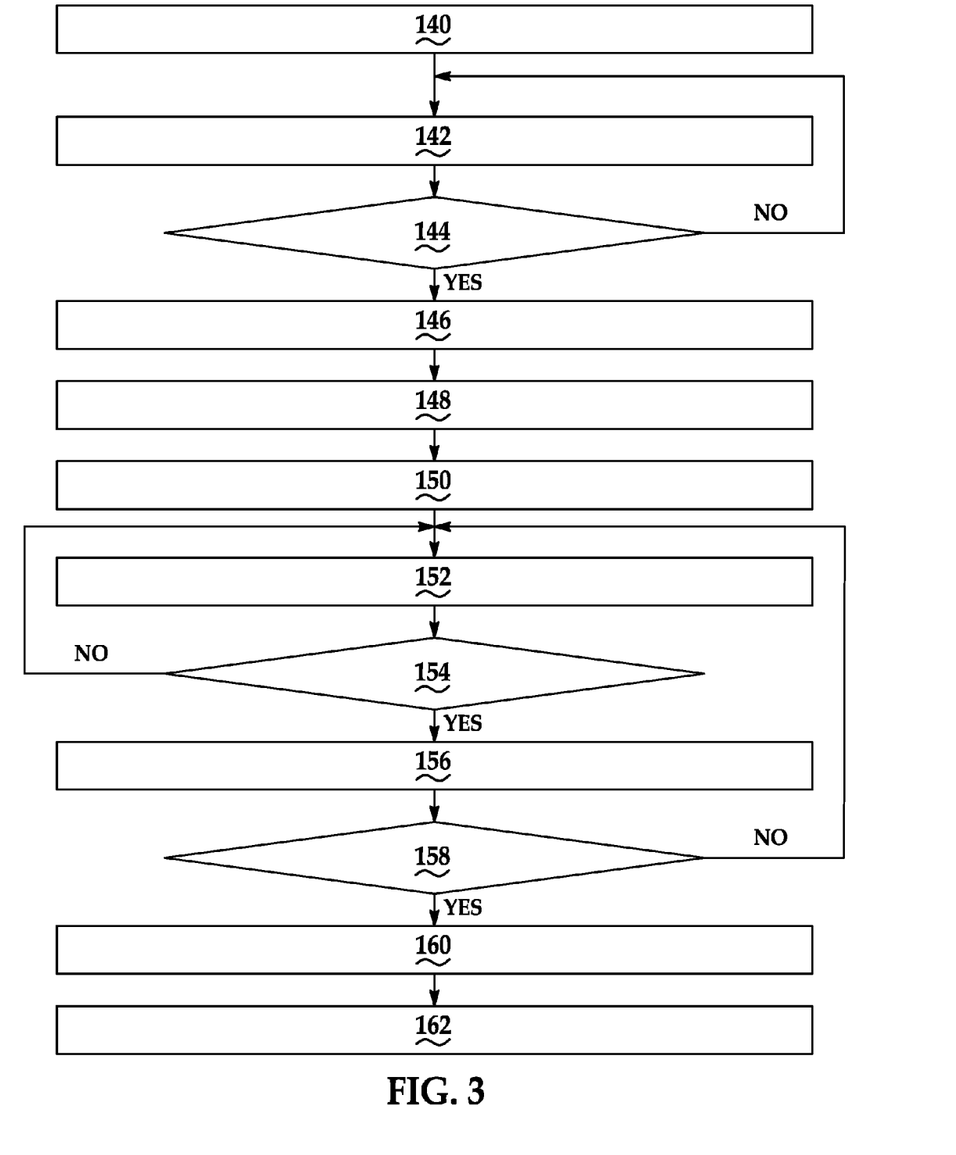
FIG. 3 is a flowchart of a method for determining a cloud point temperature value for diesel fuel, utilizing the cloud point monitoring system of FIG. 2.

Referring to FIG. 3, a flowchart of a method for determining a cloud point temperature value for diesel fuel using the cloud point monitoring system of FIG. 2 in accordance with another exemplary embodiment will now be explained with reference to steps 140-162. At step 140, the tubular conduit 70 receives diesel fuel therein. The diesel fuel flows through tubular conduit 70 from first end 100 to second end 102 where it is in fluid communication with temperature sensor 88. At step 142, the controller 94 receives a first signal from the temperature sensor 88 indicative of a temperature of the diesel fuel in the tubular conduit 70, and determines a first temperature value based on the first signal. In one exemplary embodiment, the magnitude of the first temperature value is proportional to either an amplitude of the first signal or a frequency of the first signal. At step 144, the controller 94 makes a determination as to whether a first temperature value is within a first predetermined temperature range or, alternatively, at or below a set point temperature. This assessment of the first temperature is to determine whether the fuel temperature has reached a temperature where it is desirable to begin evaluation of the cloud point temperature. In one exemplary embodiment, the first predetermined temperature range is a temperature range greater than or equal to 10° C. Of course other temperature ranges are contemplated herein. If the value of step 144 equals "yes", the method advances to step 146. Otherwise, the method returns to step 142. At step 146, the controller 94 generates a second signal to induce the light source 80 to emit light from the first end 100 of the tubular conduit 70 toward the second end 102 of the tubular conduit 70, which is reflected from the reflective member 82 disposed proximate to the second end 102 of the tubular conduit 70 toward the light sensor 80 disposed proximate to the first end 100 of the tubular conduit 70. At step 148, the controller 94 receives a third signal from the light sensor 86 indicative of a light intensity level associated with the light received from the reflective member 82 and determines a first light intensity value based on the third signal. In one exemplary embodiment, the first light intensity value is proportional to either an amplitude of the third signal or a frequency of the third signal. At step 150, the controller 94 generates a fourth signal to induce the thermal device 84 to cool both the reflective member 82 and diesel fuel proximate to the reflective member 82. At step 152, the controller 94 receives a fifth signal from the temperature sensor 88 indicative of a temperature of the reflective member 82, and determines a second temperature value based on the fifth signal. In one exemplary embodiment, the second temperature value is proportional to either an amplitude of the fifth signal or a frequency of the fifth signal. At step 154, the controller 94 makes a determination as to whether a second temperature value is less than or equal to a previous temperature value minus 2° C. or other decrement value suitable to indicate the temperature is changing. If the value of step 154 equals "yes", the method advances to step 156. Otherwise, method returns to step 152. At step 156, the controller 94 receives a sixth signal from the light sensor 86 indicative of a light intensity level associated with the light received from the reflective member 82 and determines a second light intensity value based on the sixth signal. In one exemplary embodiment, the second light intensity value is proportional to either an amplitude of the sixth signal or a frequency of the sixth signal. At step 158, the controller 94 makes a determination as to whether the absolute value of quantity (second light intensity value−first light intensity value) is greater than a threshold light intensity difference value; indicating the diesel fuel is at a cloud point temperature. For example, when the temperature of the fuel is above the cloud point temperature, the first light intensity value and the second light intensity value are essentially the same resulting in a negligible, or even zero difference. Upon reaching the cloud point temperature, the waxy crystals which form in the fuel scatter the light beam thereby reducing the intensity of the light reflected back to light sensor 86. Thus the absolute value of the difference in the light intensity values increases at temperatures which are at or below the cloud point temperature. A threshold difference value is selected which is indicative of the cloud point temperature. If the value of step 158 equals "yes", the method advances to step 160. Otherwise, the method returns to step 152. At step 160, the controller 94 sets a cloud point temperature value equal to the second temperature value and (i) displays the cloud point temperature value on the display device 98, and (ii) stores the cloud point temperature value in the memory device 96. At step 162, the controller 94 stops generating the fourth signal to induce the thermal device 84 to stop cooling the reflective member 82. The steps of the method may be repeated continuously in conjunction with the operation of vehicle 10 or engine 20.

Figure 4:
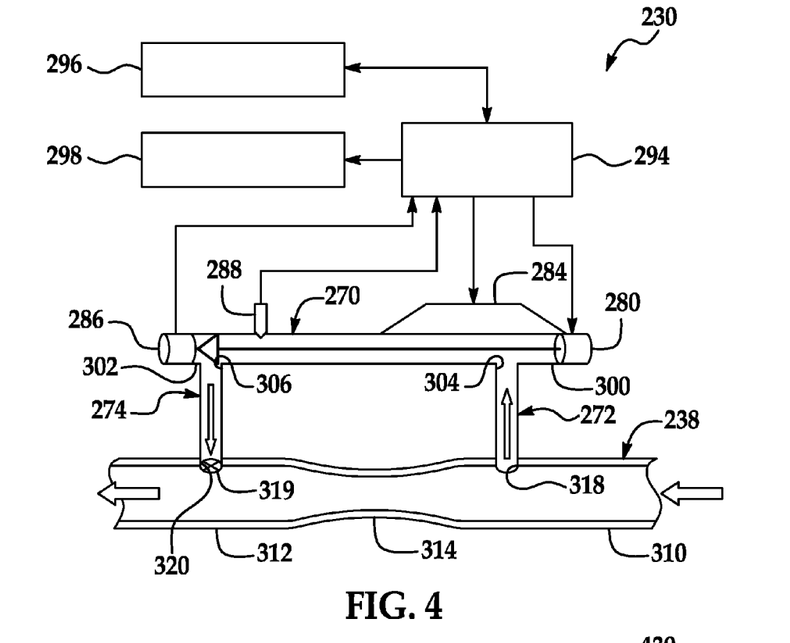
FIG. 4 is a schematic illustration of a cloud point monitoring system in accordance with a second exemplary embodiment of the invention.

Referring to FIG. 4, a second exemplary embodiment of a cloud point monitoring system 230 embodying the present invention will now be explained. The elements of system 230 are identical to and have the same function as those of system 30 above, except as noted below, and have been indexed by 200 for clarity.

In contrast to the thermal device 84 arrangement in system 30, the thermal device 284 of system 230 is disposed adjacent to the tubular conduit 270. The thermal device 284 is configured to cool the tubular conduit 270 and the diesel fuel therein along its length, and preferably proximate first end 300, and particularly the fuel proximate to thermal device 284, in response to receiving a control signal from the controller 294. In one exemplary embodiment, the thermal device 284 is a Peltier cell.

In contrast to the light sensor arrangement in system 30 above, the light sensor 286 of system 230 is coupled to the tubular conduit 270 proximate to the end 302 of the tubular conduit 270. The light sensor 286 is configured to receive a portion of the light directly from the light source 280 and to generate a signal indicative of a light intensity level associated with the received light. The signal from the light sensor 286 is sent to the controller 294.

The filter 319 is disposed over the aperture 320. The filter 319 is provided and adapted to filter wax crystals that may be formed in the diesel fuel flowing through the tubular conduit 274 in conjunction with the operation of thermal device 284.

Figure 5:
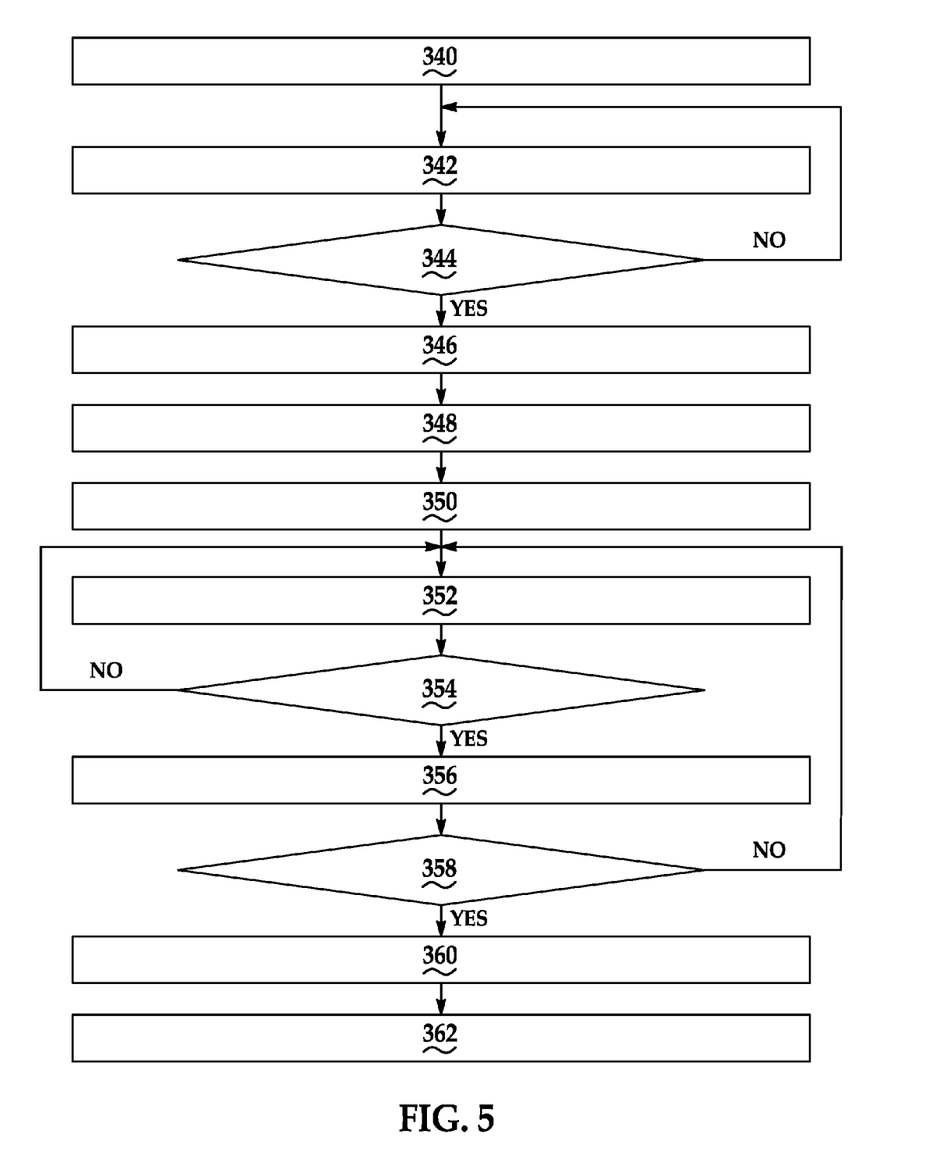
FIG. 5 is a flowchart of a method for determining a cloud point temperature value for diesel fuel, utilizing the cloud point monitoring system of FIG. 4.

Referring to FIG. 5, a flowchart of a method for determining a cloud point temperature value for diesel fuel using the cloud point monitoring system of FIG. 4 in accordance with another exemplary embodiment will now be explained. The steps of the method are analogous to and have the same purpose as the method employed with system 30 (FIG. 2) above except as noted below, and have been indexed by 200 for clarity. Steps 340, 342 and 344 are identical to steps 140, 142 and 144, respectively, excepting that they apply to the elements of system 230 rather than system 30. At step 346, the controller 294 generates a second signal to induce the light source 280 to emit light from the first end 300 of the tubular conduit directed toward the light sensor 286 disposed proximate to the second end 302 of the tubular conduit 270. Steps 348, 350, 352, 354, 356, 358, 360 and 362 are identical to steps 148, 150, 152, 154, 156, 158, 160 and 162, respectively, excepting that they apply to the elements of system 230 rather than system 30. Steps 348-362 may also be repeated continuously or otherwise in conjunction with the operation of vehicle 10 or engine 20.

Figure 6:
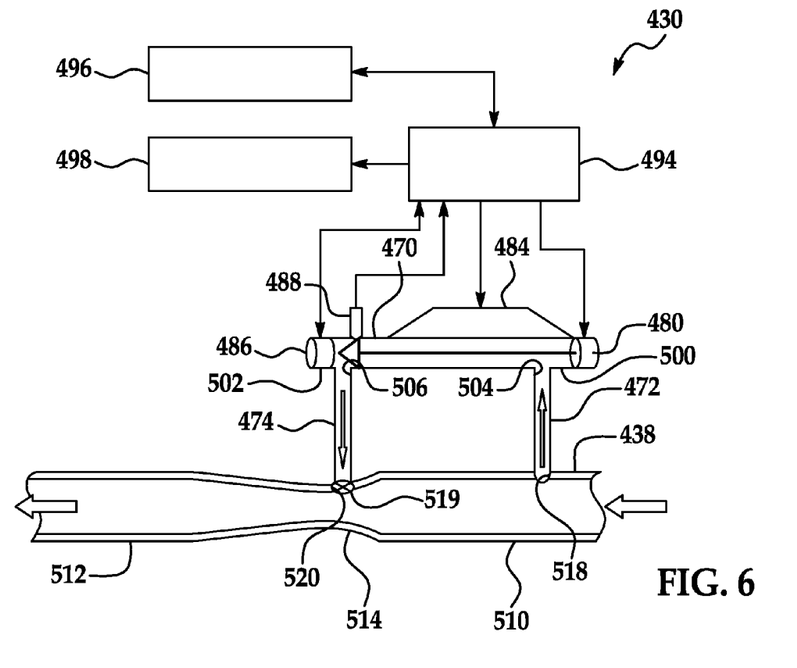
FIG. 6 is a schematic illustration of a cloud point monitoring system in accordance with a third exemplary embodiment of the invention.

Referring now to FIG. 6, a third exemplary embodiment of a cloud point monitoring system 430 embodying the present invention will now be explained. The elements of system 430 are identical to and have the same function as those of system 230 above except as noted below, and have been indexed by 200 over the elements of system 230 (FIG. 4) for clarity. The cloud point monitoring system 430 is fluidly coupled to a diesel fuel conduit 438 and receives a portion of the diesel fuel flowing through the diesel fuel conduit 438 to determine the cloud point temperature of the diesel fuel. Diesel fuel conduit 438 includes end portions 510, 512 and a venturi portion 514 disposed between the end portions 510, 512. The primary difference between the cloud point monitoring system 430 and the cloud point monitoring system 230 is that the tubular conduit 474 extends from the tubular conduit 470 to the venturi portion 514 of the diesel fuel conduit 438 (see FIG. 6), instead of the tubular conduit 274 extending from the tubular conduit 270 to the end portion 112 of the diesel fuel conduit 38 (see FIG. 4). The operational functionality of the cloud point monitoring system 430 is substantially similar to the operational functionality of the cloud point monitoring system 230. The restricted portion 514 of fuel conduit 438 acts as a flow induction mechanism to induce flow of a portion of the fuel supply available in conduit 438 through conduits 472, 470 and 474.

Figure 7:
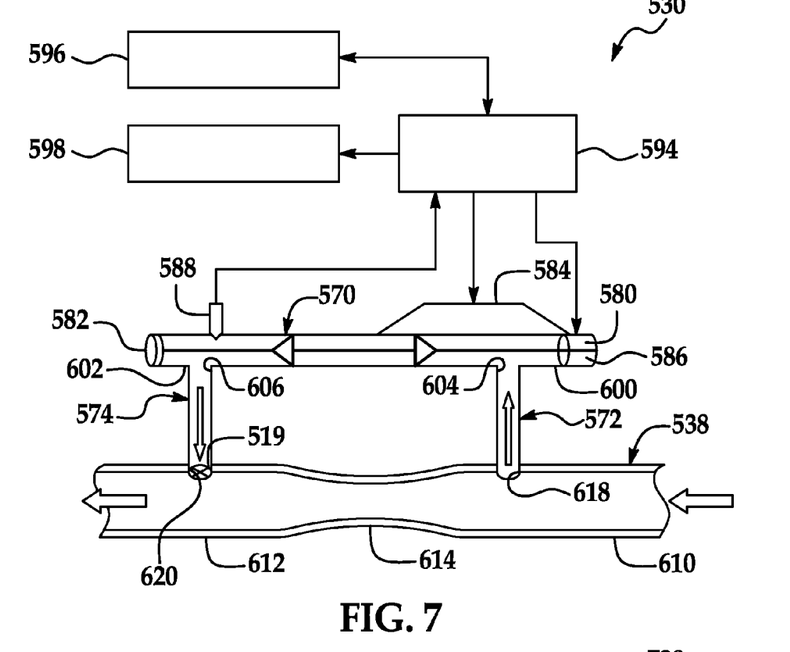
FIG. 7 is a schematic illustration of a cloud point monitoring system in accordance with a fourth exemplary embodiment of the invention.

Referring to FIG. 7, a fourth exemplary embodiment of a cloud point monitoring system 530 embodying the present invention will now be explained. The elements of system 530 are identical to and have the same function as those of system 230 above except as noted below, and have been indexed by 300 over the elements of system 230 for clarity. The principal distinction between cloud point monitoring system 530 and system 230 relates to the incorporation of reflective member 582 and the location of light sensor 586.

The reflective member 582 of system 530 is coupled to the tubular conduit 570 proximate to the second end 602 of the tubular conduit 570. The reflective member 582 is configured to receive a portion of the light from the light source 580 and to reflect the portion of light back toward the first end 600 of the tubular conduit 570. In one exemplary embodiment, the reflective member 582 is a mirror.

The thermal device 584 of system 530 is disposed adjacent to the tubular conduit 570 along its length and preferably proximate first end 600. The thermal device 584 is configured to cool the tubular conduit 570 and the diesel fuel therein proximate to thermal device 584 in response to receiving a control signal from the controller 594. In one exemplary embodiment, the thermal device 584 is a Peltier cell.

The light sensor 586 is coupled to the tubular conduit 570 proximate to the end 600 of the tubular conduit 570. The light sensor 586 is configured to receive a portion of the light from the reflective member 582 and to generate a signal indicative of a light intensity level associated with the received light. The signal from the light sensor 586 is sent to the controller 594.

Figure 8:
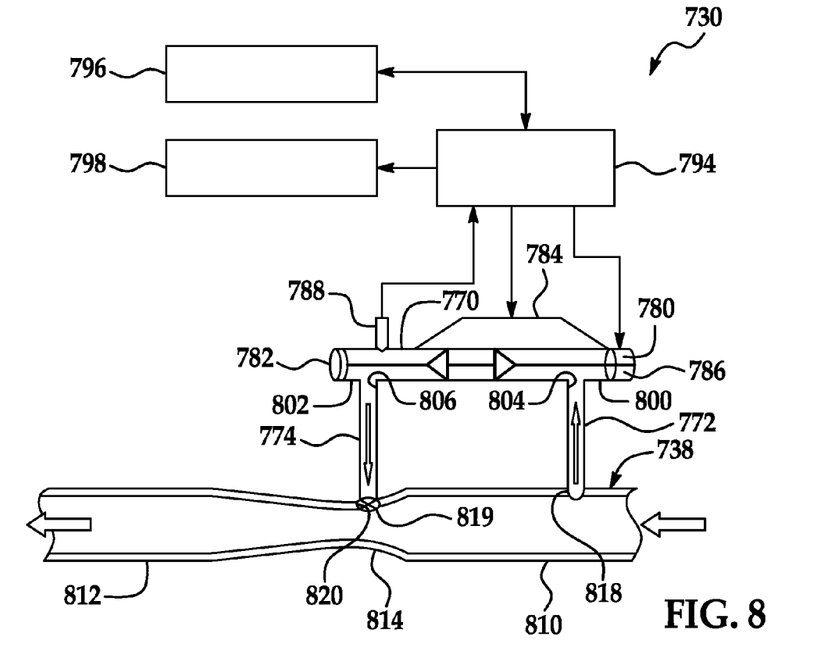
FIG. 8 is a schematic illustration of a cloud point monitoring system in accordance with a fifth exemplary embodiment of the invention.

Referring to FIG. 8, a fifth exemplary embodiment of a cloud point monitoring system 730 embodying the present invention will now be explained. The elements of system 730 are identical to and have the same function as those of system 230 above except as noted below, and have been indexed by 500 over the elements of system 230 for clarity. It should be noted that the diesel fuel conduit 738 would replace the diesel fuel conduit 238 in the vehicle 10. Further, the diesel fuel conduit 738 includes end portions 810, 812 and a venturi portion 814 disposed between the end portions 810, 812. The primary difference between the cloud point monitoring system 730 and the cloud point monitoring system 230 is that the tubular conduit 774 extends from the tubular conduit 770 to the venturi portion 814 of the diesel fuel conduit 738, instead of the tubular conduit 274 extending from the tubular conduit 270 to the end portion 212 of the diesel fuel conduit 238. The operational functionality of the cloud point monitoring system 730 is substantially similar as the operational functionality of the cloud point monitoring system 230 described above.

The cloud point monitoring systems and motor vehicles which incorporate them described herein represent a substantial advantage over other systems and methods. In particular, the cloud point monitoring systems of this invention provide a technical effect of utilizing a received light intensity level of a light beam propagating through diesel fuel, either directly to a light sensor or indirectly by reflection off a reflective member, to determine a cloud point temperature value indicating a cloud point temperature of the diesel fuel.

While the light source, light sensor, temperature sensor and thermal device are illustrated in the several exemplary embodiments in the respective positions shown with reference to the respective first ends and second ends of the first tubular conduits, it is believed that embodiments (not shown) which reverse the positions of these elements with reference to the respective ends will also function in accordance with the present invention and are within the scope thereof.

While the invention has been described with reference to exemplary embodiments, it will be understood by those skilled in the art that various changes may be made and equivalent elements may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed for carrying this invention, but that the invention will include all embodiments falling within the scope of the appended claims. Moreover, the use of the terms, first, second, etc. are used to distinguish one element from another. Furthermore, the use of the terms a, an, etc. do not denote a limitation of quantity, but rather denote the presence of at least one of the referenced items.

What is claimed is:

1. A cloud point monitoring system, comprising:
   a first conduit, having a first aperture and a second aperture, in fluid communication with a fuel conduit to allow a portion of a diesel fuel supply in the fuel conduit to enter the first aperture, flow in the first conduit and exit the second aperture;
   a light source disposed in the first conduit, the light source configured to emit light in the first conduit in response to a first signal;
   a light sensor disposed in the first conduit and spaced from the light source, the light sensor configured to receive at least a portion of the light and to generate a second signal indicative of a light intensity level;
   a temperature sensor disposed on the first conduit and configured to generate a third signal indicative of a temperature of the diesel fuel supply in the first conduit; and
   a controller configured to generate the first signal to induce the light source to emit light, the controller further configured to receive the second signal from the light sensor and the third signal from the temperature sensor and to determine a cloud point temperature value associated with the diesel fuel supply based on the second and third signals.

2. The cloud point monitoring system of claim 1, wherein the light source is disposed proximate the first aperture, further comprising a reflective member disposed proximate to the second aperture and configured to receive light emitted by the light source and reflect it toward the light sensor, and a thermal device disposed adjacent said reflective member the thermal device configured to cool the reflective member in response to a fourth signal from the controller.

3. The cloud point monitoring system of claim 1, further comprising a thermal device disposed proximate the first conduit and configured to cool the first conduit in response to a fourth signal from the controller.

4. The cloud point monitoring system of claim 1, wherein the light source is disposed proximate to the first aperture and configured to emit the light toward the second aperture in response to the first signal, the cloud point monitoring system further having a reflective member disposed proximate to the second aperture and configured to receive the light from the light source and to reflect at least a portion of the light toward the first aperture.

5. The cloud point monitoring system of claim 4, wherein the light sensor is disposed proximate to the first aperture and configured to receive the portion of the light from the reflective member and to generate the second signal indicative of the light intensity level associated with the portion of the light received from the reflective member.

6. The cloud point monitoring system of claim 1, wherein the light sensor is disposed proximate to the second aperture and configured to receive at least a portion of the light from the light source and to generate the second signal indicative of the light intensity level associated with the portion of light received from the light source.

7. The cloud point monitoring system of claim 1, further comprising second and third conduits, the fuel conduit having first and second end portions and a restricted portion, the restricted portion being disposed between the first and second end portions, the second conduit routing the portion of the diesel fuel supply from the first end portion of the fuel conduit through the first aperture into the first conduit, the third conduit routing the diesel fuel supply in the first conduit from the second aperture to the second end portion of the fuel conduit.

8. The cloud point monitoring system of claim 7, further comprising a filter in fluid communication with the third conduit operative to filter the diesel fuel supply.

9. The cloud point monitoring system of claim 1, further comprising second and third conduits, the fuel conduit having a first end portion and a venturi portion, the second conduit routing the portion of the diesel fuel supply from the first end portion of the fuel conduit through the first aperture into the first conduit, the third conduit routing the portion of diesel fuel supply in the first conduit from the second aperture to the venturi portion of the fuel conduit.

10. The cloud point monitoring system of claim 9, further comprising a filter in fluid communication with the third conduit operative to filter the diesel fuel supply.

11. The cloud point monitoring system of claim 1, wherein the light source is configured to produce a coherent light beam or a focused light beam.

12. A motor vehicle, comprising:
    a diesel engine configured to receive diesel fuel from a fuel tank; and
    a cloud point monitoring system in fluid communication with the fuel tank and configured to receive a portion of the diesel fuel from the fuel tank, the cloud point monitoring system comprising:
    a first conduit, having a first aperture and a second aperture in fluid communication with a fuel conduit to allow a portion of a diesel fuel supply in the fuel conduit to enter the first aperture, flow in the first conduit and exit the second aperture;
    a light source disposed in the first conduit, the light source configured to emit light in the first conduit in response to a first signal;
    a light sensor disposed in the first conduit and spaced from the light source, the light sensor configured to receive at least a portion of the light and to generate a second signal indicative of a light intensity level;
    a temperature sensor disposed on the first conduit and configured to generate a third signal indicative of a temperature of the portion of the diesel fuel supply in the first conduit; and
    a controller configured to generate the first signal to induce the light source to emit light, the controller further configured to receive the second signal from the light sensor and the third signal from the temperature sensor and to determine a cloud point temperature value associated with the diesel fuel supply based on the second and third signals.

13. The motor vehicle of claim 12, wherein the light source is disposed proximate to the first aperture, and the cloud point monitoring system further has a reflective member disposed proximate to the second aperture and configured to receive light emitted by the light source and reflect it toward the light sensor, the thermal device configured to cool the reflective member in response to a fourth signal from the controller.

14. The motor vehicle of claim 12, wherein the cloud point monitoring system further has a thermal device disposed proximate the first conduit and configured to cool the first conduit in response to a fourth signal from the controller.

15. The motor vehicle of claim 12, wherein the light source is disposed proximate to the first aperture and configured to emit the light toward the second aperture in response to the first signal, the cloud point monitoring system further having a reflective member disposed proximate to the second aperture and configured to receive the light from the light source and to reflect at least a portion of the light toward the first aperture.

16. The motor vehicle of claim 15, wherein the light sensor is disposed proximate to the first aperture configured to receive the portion of the light from the reflective member and to generate the second signal indicative of the light intensity level associated with the portion of the light received from the reflective member.

17. The motor vehicle of claim 12, wherein the light sensor is disposed proximate to the second aperture and configured to receive at least a portion of the light from the light source and to generate the second signal indicative of the light intensity level associated with the portion of light received from the light source.

18. The motor vehicle of claim 12, further comprising a second and third conduits, the fuel conduit having first and second end portions and a restricted portion, the restricted portion being disposed between the first and second end portions, the second conduit routing the portion of the diesel fuel from the first end portion of the fuel conduit through the first aperture into the first conduit, the third conduit routing the diesel fuel in the first conduit from the second aperture to the second end portion of the fuel conduit.

19. The motor vehicle of claim 12, further comprising second and third conduits, the fuel conduit having a first end portion and a venturi portion, the second conduit routing the portion of the diesel fuel from the first end portion of the fuel conduit through the first aperture into the first conduit, the third conduit routing the portion of the diesel fuel in the first conduit from the second aperture to the venturi portion of the fuel conduit.

20. The motor vehicle of claim 12, wherein the light source is configured to produce a coherent light beam or a focused light beam.

* * * * *